United States Patent
Du

(10) Patent No.: US 12,004,898 B2
(45) Date of Patent: Jun. 11, 2024

(54) ULTRASOUND GRAY-SCALE IMAGING SYSTEM AND METHOD

(71) Applicant: Shenzhen Mindray Bio-Medical Electronics Co., Ltd., Shenzhen (CN)

(72) Inventor: Yigang Du, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 18/141,691

(22) Filed: May 1, 2023

(65) Prior Publication Data

US 2023/0380795 A1    Nov. 30, 2023

Related U.S. Application Data

(63) Continuation of application No. 15/912,182, filed on Mar. 5, 2018, which is a continuation of application No. PCT/CN2015/088985, filed on Sep. 6, 2015.

(51) Int. Cl.
| | |
|---|---|
| *A61B 8/06* | (2006.01) |
| *A61B 8/00* | (2006.01) |
| *A61B 8/08* | (2006.01) |
| *G01S 15/89* | (2006.01) |
| *A61B 6/00* | (2024.01) |

(52) U.S. Cl.
CPC ............... *A61B 8/06* (2013.01); *A61B 8/461* (2013.01); *A61B 8/5246* (2013.01); *G01S 15/8906* (2013.01); *G01S 15/8979* (2013.01); *A61B 6/547* (2013.01); *A61B 8/5207* (2013.01); *G01S 15/8927* (2013.01)

(58) Field of Classification Search
CPC .............................. A61B 8/5247; A61B 8/06
See application file for complete search history.

(56) References Cited

U.S. PATENT DOCUMENTS

| | | | |
|---|---|---|---|
| 6,074,348 A * | 6/2000 | Chiao ................. | G01S 15/8993 600/443 |
| 6,116,244 A * | 9/2000 | Hossack ............... | A61B 8/483 600/441 |
| 6,309,356 B1 | 10/2001 | Ustuner et al. | |
| 6,406,430 B1 * | 6/2002 | Ishrak ................. | G01S 7/52039 600/441 |
| 6,517,489 B1 | 2/2003 | Phillips et al. | |
| 6,551,246 B1 | 4/2003 | Ustuner et al. | |

(Continued)

FOREIGN PATENT DOCUMENTS

| | | |
|---|---|---|
| CN | 103181788 A | 7/2013 |
| CN | 103492855 A | 1/2014 |

(Continued)

OTHER PUBLICATIONS

Lovstakken, L., Bjaerum, S., Martens, D., & Torp, H. (2006). Blood flow imaging-a new real-time, flow imaging technique. IEEE transactions on ultrasonics, ferroelectrics, and frequency control, 53(2), 289-299. (Year: 2006).*

(Continued)

*Primary Examiner* — Keith M Raymond
*Assistant Examiner* — Johnathan Maynard
(74) *Attorney, Agent, or Firm* — Kory D. Christensen

(57) ABSTRACT

An non-Doppler flow imaging system is disclosed that overlays a B-flow imaging sequence over B-mode ultrasound image data.

18 Claims, 7 Drawing Sheets

(56) References Cited

U.S. PATENT DOCUMENTS

| | | | |
|---|---|---|---|
| 6,589,177 B1 * | 7/2003 | Detmer | G01S 7/52066 600/443 |
| 10,624,612 B2 | 4/2020 | Sumi et al. | |
| 2001/0020129 A1 | 9/2001 | Hwang et al. | |
| 2006/0173313 A1 | 8/2006 | Liu et al. | |
| 2006/0241429 A1 | 10/2006 | Ustuner et al. | |
| 2007/0038115 A1 | 2/2007 | Quigley et al. | |
| 2007/0242567 A1 | 10/2007 | Daft et al. | |
| 2008/0086054 A1 * | 4/2008 | Slayton | A61B 8/14 600/438 |
| 2009/0326379 A1 | 12/2009 | Daigle et al. | |
| 2011/0301470 A1 * | 12/2011 | Sato | A61B 8/13 600/463 |
| 2012/0172725 A1 * | 7/2012 | Wang | A61B 8/06 600/443 |
| 2012/0296215 A1 | 11/2012 | Brown et al. | |
| 2013/0245441 A1 * | 9/2013 | Datta | A61B 8/0883 600/438 |
| 2014/0371594 A1 * | 12/2014 | Flynn | A61B 8/06 600/454 |
| 2015/0141832 A1 * | 5/2015 | Yu | G01S 7/52085 600/455 |
| 2015/0342567 A1 | 12/2015 | Ustuner et al. | |
| 2015/0359512 A1 | 12/2015 | Boctor et al. | |
| 2016/0066888 A1 * | 3/2016 | Yao | A61B 8/481 600/431 |
| 2016/0089108 A1 * | 3/2016 | Kim | G01S 7/52066 600/443 |
| 2019/0129026 A1 | 5/2019 | Sumi et al. | |

FOREIGN PATENT DOCUMENTS

| | | | | |
|---|---|---|---|---|
| EP | 1122556 A2 * | 8/2001 | ............... | A61B 8/06 |
| JP | 2002034987 A * | 2/2002 | | |
| JP | 2002034987 A | 2/2002 | | |
| JP | 4746758 B2 * | 8/2011 | ............... | A61B 8/06 |
| WO | WO-2013154229 A1 * | 10/2013 | ............... | A61B 8/06 |

OTHER PUBLICATIONS

Chiao, R. Y., Mo, L. Y., Hall, A. L., Miller, S. C., & Thomenius, K. E. (Oct. 2000). B-mode blood flow (B-flow) imaging. In 2000 IEEE Ultrasonics Symposium. Proceedings. An International Symposium (Cat. No. 00CH37121) (vol. 2, pp. 1469-1472). IEEE. (Year: 2000).*

Weskott, H. P. (2000). B-Flow-eine neue Methode zur Blutflussdetektion. Ultraschall in der Medizin, 21(02), 59-65. (Year: 2000).*

Umemura, A., & Yamada, K. (2001). B-mode flow imaging of the carotid artery. Stroke, 32(9), 2055-2057. (Year: 2001).*

Cheung, C. C., Alfred, C. H., Salimi, N., Yiu, B. Y., Tsang, I. K., Kerby, B., . . . & Dickie, K. (2012). Multi-channel pre-beamformed data acquisition system for research on advanced ultrasound imaging methods. IEEE transactions on ultrasonics, ferroelectrics, and frequency control, 59(2), 243-253. (Year: 2012).*

Lockwood, G. R., Talman, J. R., & Brunke, S. S. (1998). Real-time 3-D ultrasound imaging using sparse synthetic aperture beamforming. IEEE transactions on ultrasonics, ferroelectrics, and frequency control, 45(4), 980-988. (Year: 1998).

* cited by examiner

ULTRASOUND GRAY-SCALE IMAGING SYSTEM AND METHOD

CROSS-REFERENCE TO RELATED APPLICATIONS

This application is a continuation-in-part of U.S. patent application Ser. No. 15/912,182, filed Mar. 5, 2108, for "Ultrasound Gray-Scale Imaging System and Method," which is a continuation of Patent Cooperation Treaty Application No. PCT/CN2015/088985, filed Sep. 6, 2015, for "Ultrasound Gray-Scale Imaging System and Method," both of which are incorporated herein by reference.

TECHNICAL FIELD

The present disclosure relates to ultrasound imaging system, and more particularly to ultrasound flow imaging systems and methods which use grayscale images to represent the flow of liquid.

SUMMARY

Ultrasound flow imaging methods and systems which use grayscale images to represent the flow of liquid are provided.

DETAILED DESCRIPTION

Figure 1A:
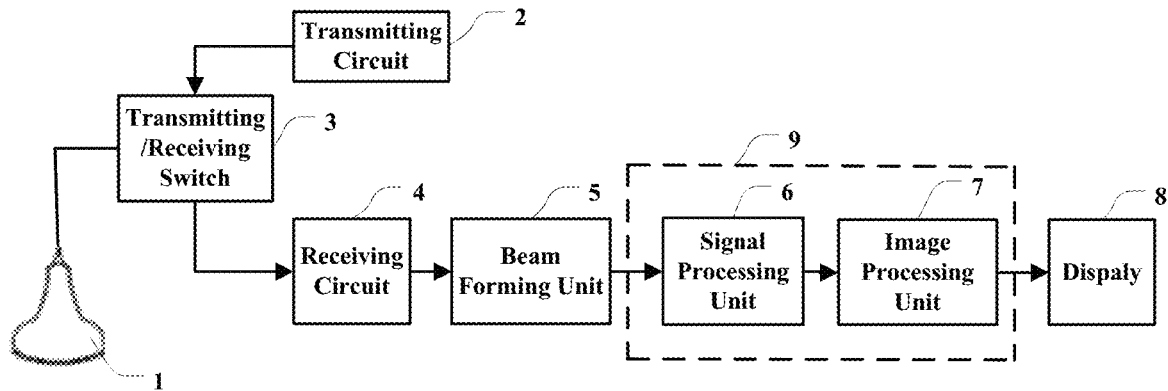
FIG. 1A, FIG. 1B, FIG. 1C and FIG. 1D are block diagrams of embodiments of ultrasound grayscale imaging systems.

Grayscale flow imaging (e.g., B-flow imaging) is an ultrasound flow imaging method in which the ordinary B-mode signals are processed to display blood flow using grayscale images without the use of Doppler processing. Traditional grayscale flow imaging methods use focused ultrasound waves and scan line by line, thereby having high flow accuracy and high sensitivity. The flow signals in blood vessels can be enhanced by wall filtering, and then, in connection with the tissue signals, the wall of the blood vessels and the flowing of the red blood cells in the blood vessels may be simultaneously displayed in grayscale images. The dynamic images obtained by the grayscale flow imaging can intuitively display the blood flow and the stationary tissues. However, since the traditional grayscale flow imaging methods, like B-flow imaging, use focused ultrasound waves and scan line by line, the time resolution of the images will be decreased, reducing the quality of the grayscale flow images. When the velocity of the blood flow is too high, since there is a scanning time interval between each two scanning lines, the images of the grayscale flow imaging will be distorted.

In one embodiment, an ultrasound grayscale imaging system is provided, which solves the aforementioned distortion problem. The system may include: a probe; a transmitting circuit which excites the probe to transmit multiple groups of non-focused ultrasound beams to a flow (e.g., blood flow); a receiving circuit which receives echoes of the multiple groups of non-focused ultrasound beams returned from the flow to obtain multiple groups of non-focused ultrasound echo signals; a signal processing unit which obtains flow data according to the multiple groups of non-focused ultrasound echo signals; an image processing unit which obtains B-mode ultrasound image sequence according to the flow data without Doppler processing; and a display device which displays the B-mode ultrasound image sequence.

In one embodiment, an ultrasound grayscale imaging system is provided, which may include: a probe; a transmitting circuit which excites the probe to transmit multiple groups of non-focused ultrasound beams and focused ultrasound beams to a scanning target containing a flow; a receiving circuit which receives echoes of the multiple non-focused ultrasound beams returned from the flow to obtain multiple groups of non-focused ultrasound echo signals and receives echoes of the multiple focused ultrasound beams returned from the scanning target to obtain multiple groups of focused ultrasound echo signals; a signal processing unit which obtains flow data according to the multiple groups of non-focused ultrasound echo signals without Doppler processing; a B-mode signal processing unit which obtains ultrasound image data according to the multiple groups of focused ultrasound echo signals; an image processing unit which overlays the flow data on the ultrasound image data and obtains B-mode ultrasound image sequence according to the ultrasound image data overlaid with the flow data; and a display device which displays the B-mode ultrasound image sequence.

In one embodiment, an ultrasound grayscale imaging method is provided, which may include: transmitting multiple groups of non-focused ultrasound beams to a flow; receiving echoes of the multiple groups of non-focused ultrasound beams to obtain multiple groups of non-focused ultrasound echo signals; obtaining flow data according to the multiple groups of non-focused ultrasound echo signals without Doppler processing; obtaining B-mode ultrasound image sequence according to the flow data; and displaying the B-mode ultrasound image sequence.

In the present disclosure, non-focused waves (e.g., plane waves or diffused waves) may be used, and multiple scan lines or even one whole frame of image may be obtained by one transmission. Therefore, the time resolution of the ultrasound images may be greatly increased, and the distortion issues in imaging high velocity flow in traditional grayscale flow imaging may be overcome.

FIG. 1A schematically shows a block diagram of a B-mode ultrasound grayscale imaging system in one embodiment. As shown in FIG. 1A, the ultrasound grayscale imaging system may include a probe 1, a transmitting circuit 1, a transmitting/receiving switch 3, a receiving circuit 4, a beam forming unit 5, a signal processing unit 6, an image processing unit 7 and a display device 8. The beam forming unit 5, the signal processing unit 6, and the image processing unit 7 may be implemented using any suitable combination of hardware, software, and/or firmware. For example, the aforementioned units may be implemented using one or more processors, which execute instructions stored in a non-transitory computer-readable medium.

When performing the imaging, the transmitting circuit 2 may transmit transmission pulses which are delay-focused and have a certain amplitude and polarity to the probe 1 through the transmitting/receiving switch 3. The probe 1 may be excited by the transmission pulses and transmit ultrasound waves to a scanning target containing, for example, blood flow. After a certain time interval, the probe 1 may receive ultrasound echoes reflected from the target area which contain information concerning the flow and convert the ultrasound echoes into electric signals. The scanning target may include the blood vessels in organs or tissues in a human or animal body or other vessels in organism in which flows exist, which are not shown in the figure. The flow may include the liquid existing in the blood vessels, lymphatic system or other tissues in a human or animal body or flowing liquid in other vessels in a human or animal body, which is not shown in the figure.

The receiving circuit may receive the electric signals generated by the probe 1 to obtain ultrasound echo signals and send the ultrasound echo signals to the beam forming unit 5. The beam forming unit 5 may perform focus delay, weighting, channel summation and/or other processing on the ultrasound echo signals, and then send the ultrasound echo signals to the signal processing unit 6 where signal detection, signal enhancement and/or other signal processing may be performed on the ultrasound echo signals to obtain flow data containing information about the flow without Doppler processing.

By contrast, the Doppler flow detectors leverage the Doppler shift, which is a change in the wavelength (frequency) of a Doppler pulse resulting from motion of a source, receiver or reflector. As the ultrasound transducer is both a stationary source and a receiver of sound, the Doppler shift arises from reflectors (e.g., blood) in motion. However, Doppler flow detection suffers from random noise and blooming, as well as aliasing and motion artifacts. For example, aliasing and motion artefacts occur when the pulse repetition frequency (PRF) is set too low. Therefore, Doppler processing is extremely sensitive to the selected ultrasound settings. Even so, some Doppler artifacts, like mirror and reverberation artefacts, cannot be eliminated, making Doppler processing unsuitable in some cases.

The image processing unit 7 may perform different data conversion on the flow data based on the imaging mode desired by the user to obtain image data of different modes. Thereafter, logarithmic compression, dynamic range adjustment, digital scan conversion and other processing may be performed on the image data to obtain B-mode ultrasound images in different modes. A series of ultrasound images may be obtained according to an ultrasound acquisition time sequence, which will be referred to as an ultrasound image sequence in the present disclosure. The image processing unit 7 may send the obtained ultrasound image sequence to the display device 8 where the ultrasound image sequence are displayed, thereby obtaining images representing the dynamic flow of liquid.

The probe 1 may include multiple transducers arranged in array. In each transmission of the ultrasound waves, all of, or a part of, the transducers of the probe 1 may be used. Each or each part of the used transducers may respectively be excited by the transmission pulses to respectively transmit the ultrasound waves. The ultrasound waves transmitted by these transducers may superimpose with each other during the propagation, thereby forming resultant ultrasound beam transmitted to the flow. The direction of the resultant ultrasound beam may be the transmission direction mentioned in the present disclosure. The used transducers may be excited by the transmission pulses simultaneously. Alternatively, there may be certain time delays between the excitation of the transducers used in the transmission of the ultrasound waves by the transmission pulses. By controlling the time delays between the excitation of the transducers used in the transmission of the ultrasound waves by the transmission pulses, the propagation direction of the resultant ultrasound beam may be changed. The superimposition mentioned herein may be ordinary addition or addition with a certain weight.

Figure 4:
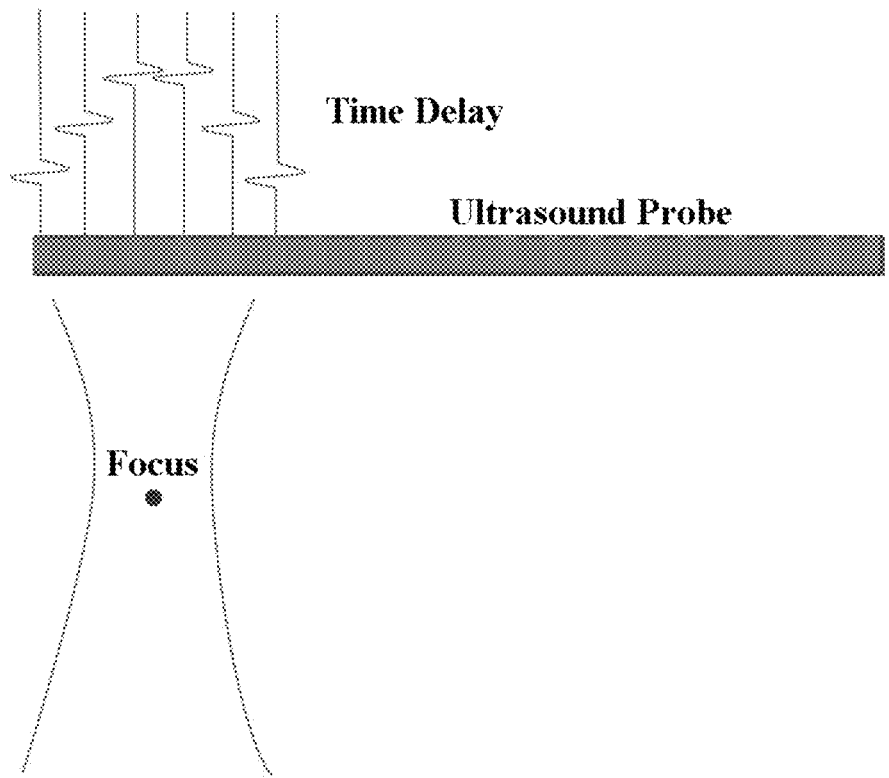
FIG. 4 schematically shows a focused ultrasound beam in one embodiment.

By controlling the time delays between the excitation of the transducers to be used in the transmission of the ultrasound waves by the transmission pulses, the ultrasound waves transmitted by the transducers may be overlaid at a pre-determined location, such that the strength of the ultrasound waves at said pre-determined location is greatest. In other words, the ultrasound waves transmitted by the transducers may be "focused" at said pre-determined location. This pre-determined location may be referred to as the "focus". This way, the obtained resultant ultrasound beam is a beam focused at the focus, which will be referred to as a "focused ultrasound beam" herein. For example, FIG. 4 schematically shows the transmission of the focused ultrasound beam. In this case, the transducers used in the transmission of the ultrasound waves (in FIG. 4, only a part of the transducers in the probe 1 are used in the transmission of the ultrasound waves) may work in a pre-determined transmission time delay (i.e., there are pre-determined time delays between the excitation of the transducers to be used in the transmission of the ultrasound waves by the transmission pulses), and the ultrasound waves transmitted by the transducers may be focused at the focus, thereby forming the focused ultrasound beam.

Alternatively, by controlling the time delays between the excitation of the transducers to be used in the transmission of the ultrasound waves by the transmission pulses, the ultrasound waves transmitted by the transducers used in the transmission of the ultrasound waves may not be focused, nor be diffused completely, but form a plane wave which is substantially planar as a whole. In the present disclosure, such plane wave without focus is referred to as "plane ultrasound beam." Conventional grayscale (non-Doppler) flow imaging techniques like B-flow imaging do not use plane ultrasound beams.

Alternatively, by controlling the time delays between the excitation of the transducers to be used in the transmission of the ultrasound waves by the transmission pulses, the ultrasound waves transmitted by the transducers used in the transmission of the ultrasound waves may be diffused during the propagation thereof, thereby forming a substantially diffused wave. In the present disclosure, such diffused wave is referred to as "diffused ultrasound beam." FIG. 5 schematically shows a diffused ultrasound beam.

Figure 2:
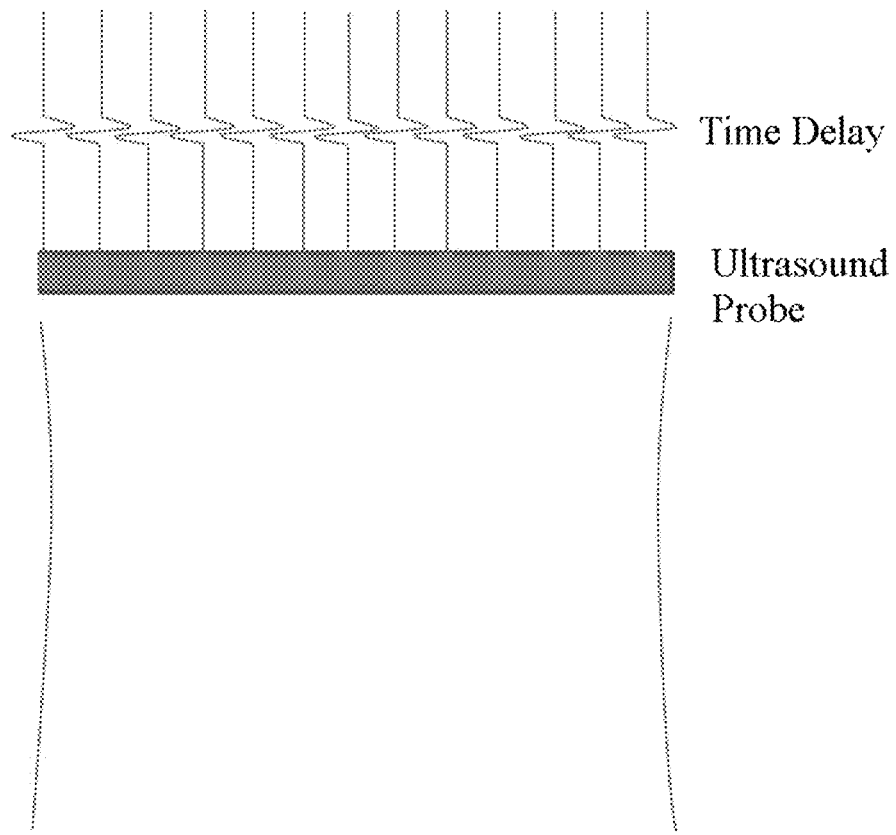
FIG. 2 schematically shows a plane ultrasound beam transmitted vertically in one embodiment.
Figure 3:
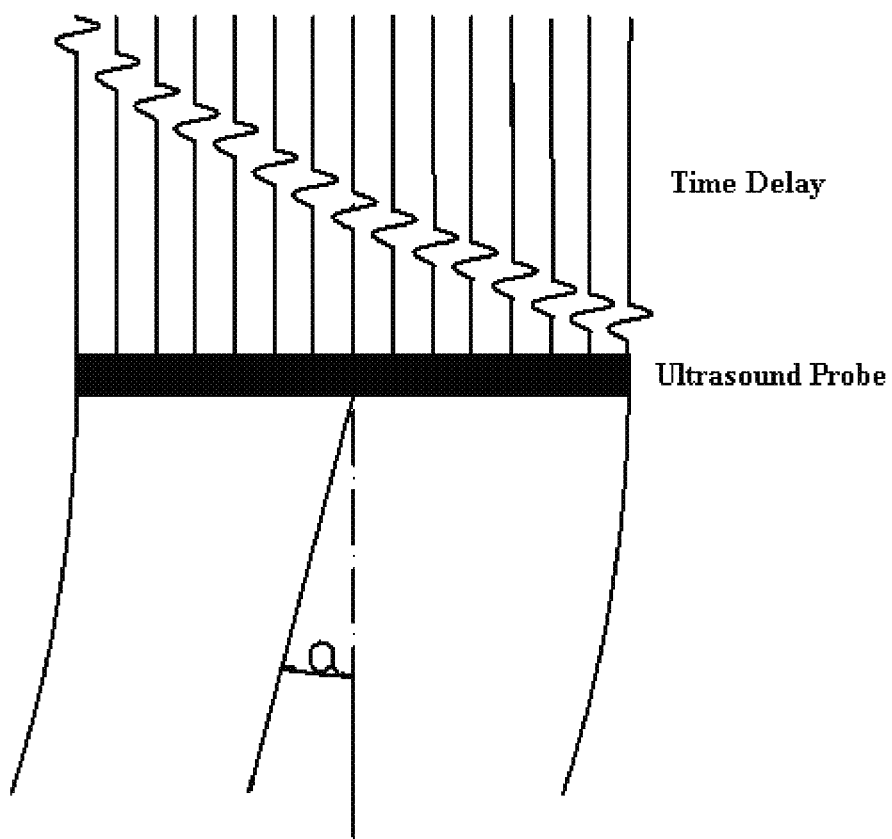
FIG. 3 schematically shows the plane ultrasound beam transmitted with a steered angle in one embodiment.

Multiple transducers arranged linearly may be excited simultaneously by electric pulse signals and simultaneously transmit ultrasound waves, and the transmission direction of the resultant ultrasound beam may be the normal direction of the plane on which the transducers are arranged. For example, FIG. 2 shows a plane wave transmitted vertically. In this case, there is no time delays between the transducers used in the transmission of the ultrasound waves (i.e., there is no time delay between the excitation of the transducers by the transmission pulses). The transducers are simultaneously excited by the transmission pulses and the ultrasound beam generated thereby is a plane wave, i.e. a plane ultrasound beam. The propagation of this plane ultrasound beam is substantially vertical to the surface from which the ultrasound waves are transmitted, i.e., the angle between the propagation direction of this plane ultrasound beam and the normal direction of the plane on which the transducers are arranged is zero. However, in the case that there are time delays between the excitation pulses applied to the transducers, the transducers will successively transmit ultrasound waves according to such time delays, and there may be a certain angle between the propagation direction of the resultant ultrasound beam and the normal direction of the plane on which the transducers are arranged, which is the steered angle of the resultant beam. By changing the time delays, the size of the steered angle of the resultant beam and the steered direction of the resultant beam in the scanning plane thereof with respect to the normal direction of the plane on which the transducers are arranged. For example, FIG. 3 shows a steered plane wave. In this case, there are pre-determined time delays between the transducers used in the transmission of the ultrasound waves (i.e., there are pre-determined time delays between the excitation of the transducers by the transmission pulses), and the transducers are excited by the transmission pulses in a pre-determined order. The ultrasound beam generated thereby may be a plane wave, i.e. a plane ultrasound beam, and there may be a certain angle (e.g., the angle α in FIG. 3) between the propagation direction of this plane ultrasound beam and the normal direction of the plane on which the transducers of the probe 1 are arranged. This angle may be the steered angle of this plane ultrasound beam. The size of the angle α may be adjusted by changing the time delays.

Figure 5:
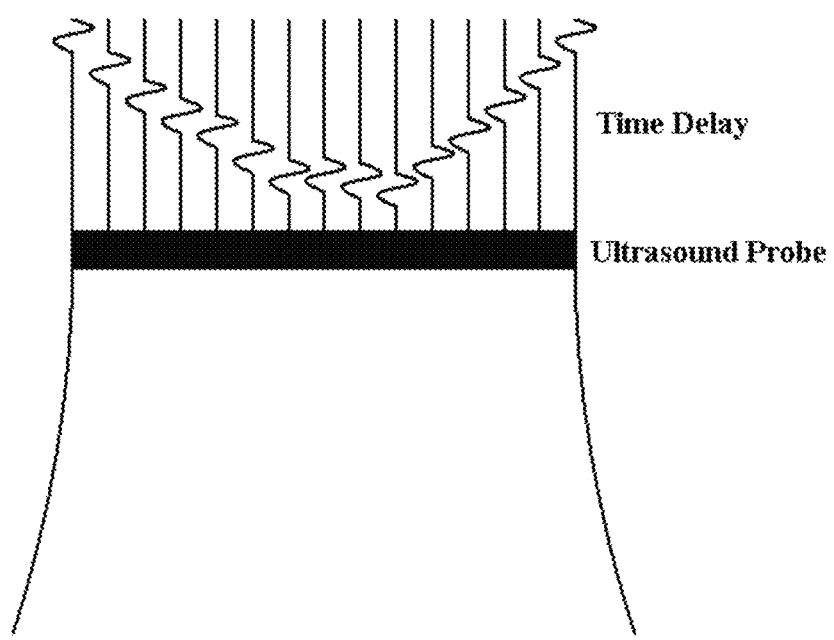
FIG. 5 schematically shows a diffused ultrasound beam in one embodiment.

In addition, as shown in FIG. 5, the diffused ultrasound beam may be considered as a non-focused wave whose virtual focus is located behind the probe. Therefore, by adjusting the time delays between the excitation of the transducers used in the transmission of the ultrasound waves by the transmission pulses, the location of the virtual focus may be adjusted, thereby changing the transmission direction of the non-focused beam. Similarly, regardless of whether the plane ultrasound beam, the focused ultrasound beam, or the diffused ultrasound beam is used, the "steered angle" of the resultant beam between the direction of the resultant beam and the normal direction of the plane on which the transducers are arranged or the location of the virtual focus may be adjusted by adjusting the time delays between the excitation of the transducers to be used in the transmission of the ultrasound waves by the transmission pulses, thereby changing the transmission angle of the ultrasound beam. The resultant beam herein may be the plane ultrasound beam, the focused ultrasound beam, or the diffused ultrasound beam, etc. In the present disclosure, the plane ultrasound beam and the diffused ultrasound beam are collectively referred to as a "non-focused ultrasound beam."

Based on the structure shown in FIG. 1A, non-focused ultrasound beams may be used in one embodiment, which that multiple scan lines or one frame of image may be obtained by one transmission. Therefore, the frame rate may be increased by 10-100 times. A wall filtering may be performed on the acquired signals to obtain the flow signals. Compared with traditional methods in which the focused ultrasound beams are used to scan the target line by line, such that each line the scanning needs to be performed multiple times and thus the transient problem of the filter needs to be overcome, this method will be more beneficial for the acquisition of the flow signals. Therefore, the time resolution of the ultrasound image will be greatly increased, and the distortion of the traditional grayscale flow imaging when imaging flow with high velocity may be reduced. With the non-focused ultrasound beam, such as the plane ultrasound beam, each frame of image is obtained continuously and there is no transient problem in filtering. Furthermore, multiple frames of image may be used to perform the wall filtering, thereby increasing the signal-to-noise ratio without loss in frame rate. Various embodiments will be described in detail with reference to the drawings.

Based on the system shown in FIG. 1A, an ultrasound imaging method is described with reference to FIG. 6.

In step S100, the transmitting circuit 2 may excite the probe 1 to transmit multiple groups of non-focused ultrasound beams to the flow. The non-focused ultrasound beams may be plane ultrasound beams or diffused ultrasound beams.

The multiple groups of non-focused ultrasound beams may be the non-focused ultrasound beams obtained by exciting the probe chronologically. The echoes of the multiple groups of non-focused ultrasound beams reflected from the flow may be received to obtain multiple groups of ultrasound echo signals which may be used to form an image sequence in time series, thereby obtaining the source data of the dynamic images.

The receiving circuit 4 may receive the echoes of one group of non-focused ultrasound beams to obtain one group of non-focused ultrasound echo signals which may be beamformed in the beam forming unit 5. In one embodiment, each group of non-focused ultrasound beams transmitted to the flow may include multiple non-focused ultrasound beams transmitted in different transmission angles. The receiving circuit 4 may receive the echoes of the non-focused ultrasound beams transmitted in different transmission angles to obtain multiple non-focused ultrasound echo signals included in one group of non-focused ultrasound echo signals. Based on the multiple non-focused ultrasound echo signals, the non-focused ultrasound echo signals obtained from a same spatial location may be spatially compounded and then be sent to the signal processing unit 6. The echoes of the non-focused ultrasound beams with different transmission angles may be used to generate one frame of ultrasound image. Therefore, the imaging frame rate can be guaranteed, the obtained echo signal may have a higher signal-to-noise ratio, and ultrasound image data with better quality may be obtained.

In addition, in one embodiment, coded pulses with wide bandwidth may be used by the transmitting circuit 1 to excite the probe to transmit non-focused ultrasound beams to the flow. With the coded pulsed with wide bandwidth, the echo signals may be enhanced. The bandwidth mentioned herein may refer to the frequency range of the various frequency components included in the signals. The wide bandwidth may refer to that the frequency range is 3 MHz to 10 MHz or even wider.

Figure 8:
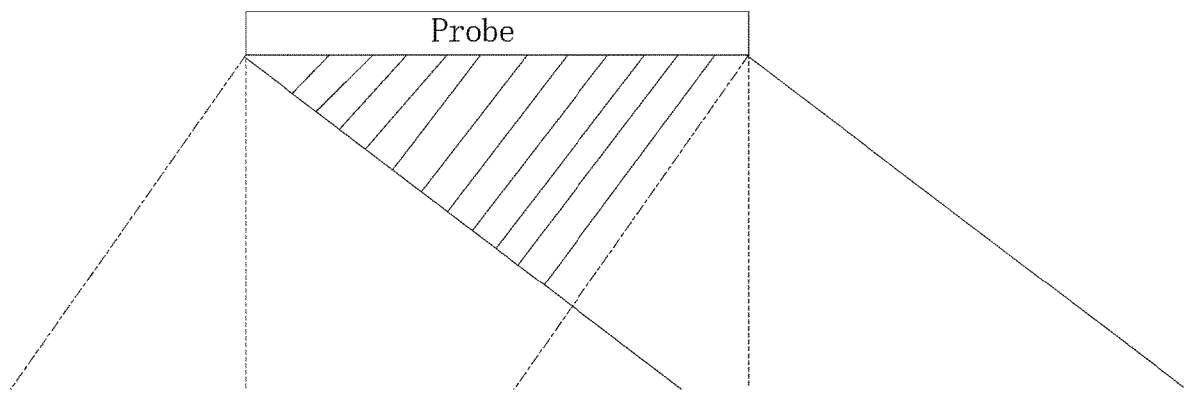
FIG. 8 schematically shows plan ultrasound beams transmitted in multiple angles in one embodiment.

In the system of FIG. 1A, each transducer of the probe may be excited by driving pulses which are a coding sequence of base sequences. Each pulse of the sequence is generally referred to as one chip. The base sequence may be obtained by phase encoding with N bit transmission code, thereby obtaining a coding sequence of N chips. These sequences may be stored in a transmission sequence memory (not shown). Each coding sequence read out from the transmission sequence memory may activate the transmitting circuit 2 in a corresponding transmission period. For example, in one embodiment, each group of non-focused ultrasound beams which the transmitting circuit 2 excites the probe 1 to transmit to the flow may include multiple transmissions to the flow, while each transmission may correspondingly obtain one non-focused ultrasound echo signals, which may be used to obtain better ultrasound image through spatial compounding. The multiple non-focused ultrasound beams transmitted to the flow may have the same or different transmission angles. In the case that each group of non-focused ultrasound beams transmitted to the flow include non-focused ultrasound beams with different transmission angles or include multiple non-focused ultrasound beams transmitted respectively in multiple different transmission angles, the non-focused ultrasound beams may be alternately transmitted to the flow according to the transmission angles or the multiple non-focused ultrasound beams may be alternately transmitted to the flow according to the transmission angles. As shown in FIG. 8, the probe 1 may transmit plane ultrasound beams to the flow in multiple angles. In FIG. 8, different lines are used to distinguish the transmissions in different angles. When the ultrasound echo signals are spatially compounded, the ultrasound echo signals in the region with hatching in FIG. 8 will be overlaid.

Figure 9:
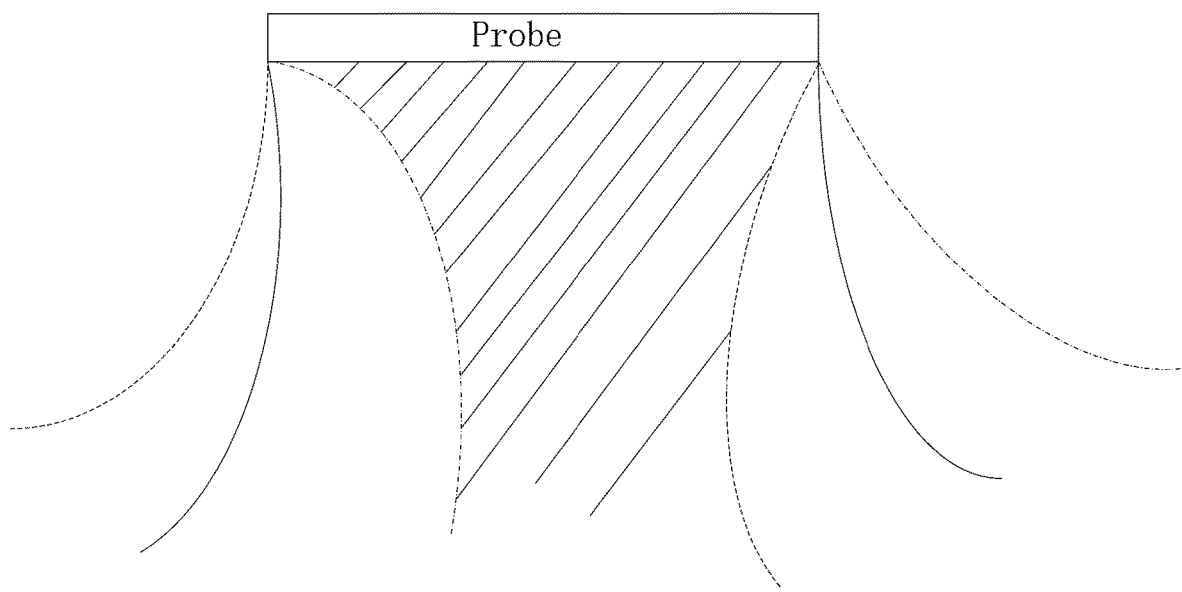
FIG. 9 schematically shows non-focused ultrasound beams transmitted in multiple angles in one embodiment.

Each group of non-focused ultrasound beams which the transmitting circuit 2 may excite the probe 1 to transmit to the flow may also include non-focused ultrasound beams with different virtual focuses. The non-focused ultrasound beams may be alternately transmitted to the flow according to the locations of the virtual focuses. Alternatively, the multiple non-focused ultrasound beams may be alternately transmitted to the flow according to the locations of the virtual focuses. For example, as shown in FIGS. 9, A, B and C are the virtual focuses, and the corresponding non-focused ultrasound beams are represented with a dashed line, a solid line and a dot-dash line, respectively. When the ultrasound echo signals are spatially compounded, the ultrasound echo signals in the region with hatching in FIG. 9 will be overlaid.

In the system as shown in FIG. 1A, the probe 1 may be excited by the pulse sequence for N times, thereby transmitting N non-focused ultrasound beams with the same waveform to the flow. The transmitting circuit 2 may drive the probe such that the ultrasound energy generated thereby is guided or manipulated to cover the whole scanning plane in one ultrasound beam. Compared with the focused ultrasound beams used in traditional grayscale flow imaging system, the frame rate may be higher, and the speed for acquiring the image data may be higher. Furthermore, by properly adjusting the time delays, the non-focused ultrasound beam may be transmitted in desired steered angle or to desired virtual focus.

In step S200, the receiving circuit 4 may receive the echoes of the multiple groups of non-focused ultrasound beams transmitted in step S100 to obtain multiple groups of non-focused ultrasound echo signals.

The ultrasound echoes generated by each ultrasound energy burst (i.e., ultrasound beam) may be reflected by the objects located on the path of each transmitted beam. The ultrasound echoes may be detected by the probe 1. Furthermore, the amplitude of the ultrasound echo signal at a certain time may represent the reflection amount at a certain location. Because of the difference of the propagation paths between the reflection point and each transducer of the probe 1, the ultrasound echoes cannot be detected simultaneously and have different amplitudes. The receiving circuit 4 may receive the electric signals generated by the probe 1 to obtain corresponding ultrasound echo signals, and send these ultrasound echo signals to the beam forming unit 5. The beam forming unit 5 may perform focus delay, weighting, and channel summation, etc. on the ultrasound echo signals. The beam forming unit 5 may track the direction of the transmitted ultrasound beam and sample the ultrasound echo signals at multiple locations along each ultrasound beam. The beam forming unit 5 may perform proper time delaying and receiving apodization on the ultrasound echo signals and sum these signals, thereby obtaining resultant ultrasound echo signals. The resultant ultrasound echo signals may accurately represent the sum of the signals of the multiple receiving channels at a certain location along one non-focused ultrasound beam. The beam forming may be implemented by setting receiving beam-former. The echo signals of the ultrasound beams transmitted in different transmission angles in the same period may be obtained by the receiving circuit. The receiving channel of the receiving circuit corresponding to each transducer may include one analog to digital converter (not shown). The proper time delay for the receiving focus may be given to each received echo signals from the memory of the receiving beam-former, and then the sum of these echo signals may be calculated to obtain the resultant echo signals. The echo signals may accurately represent the total ultrasound energy reflected from the scanning locations. For each scanning location, the time-delayed received signals may be summed in the receiving beam-former.

In one embodiment, when each group of non-focused ultrasound beams which the transmitting circuit 2 excite the probe 1 to transmit to the flow include multiple ultrasound beams transmitted in different transmission angles, the echoes of the ultrasound beams with different transmission angles may be correspondingly received to obtain multiple non-focused ultrasound echo signals. Based on the multiple non-focused ultrasound echo signals, the spatial compounding of the non-focused ultrasound echo signals obtained at the same spatial location may be performed after the beam forming.

In step S300, the signal processing unit 6 may perform signal detection and signal enhancement on the non-focused ultrasound echo signals to obtain the flow data. The signal process herein may also include logarithmic compression, etc. The signal detection herein may include envelope detection. These processes may be the common processes used in signal processing and will not be described in detail.

Figure 1B:
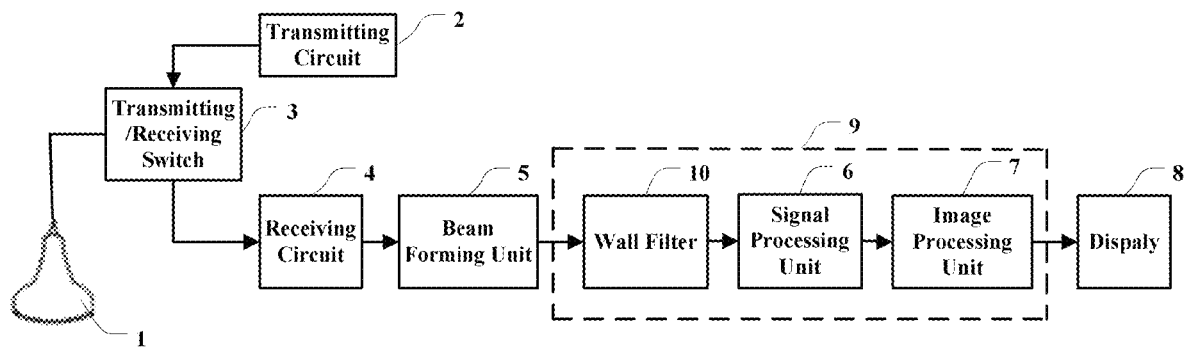

As shown in FIG. 1B, the ultrasound imaging system may further include wall filter 10. The wall filter 10 may perform wall filtering on the multiple groups of non-focused ultrasound echo signals to obtained filtered signals. The filtered signals may be sent to the signal processing unit 6 where related signal processing, such as signal detection or signal enhancement may be performed on the filtered signals to obtain wall-filtered flow data. The wall filter 10 may be traditional FIR or IIR, or more complex filter such as linear regression filter or low-rank filter, etc. In one embodiment, a high-pass filter may be used to filter the values of the non-focused ultrasound echo signals at the same location in different time, i.e., the flow signals with high frequency may be retained while the non-flow signals with low frequency will be removed. The echo signals having been wall-filtered may have higher signal-to-noise ratio, thereby obtaining higher-quality ultrasound image data.

In step S100, each group of non-focused ultrasound beams transmitted to the flow may include multiple non-focused ultrasound beams with different transmission angles. The receiving circuit 4 may receive the echoes of the multiple non-focused ultrasound beams with different transmission angles to obtain multiple non-focused ultrasound echo signals in the one group of non-focused ultrasound echo signals. Based on the multiple non-focused ultrasound echo signals, the spatial compounding may be performed on the non-focused ultrasound echo signals obtained at the same spatial location. Thereafter, the spatial-compounded echo signals may be sent to the wall filter 10.

In addition, the wall filter 10 may include two parts. The first part may be used to extract the fundamental frequency component, and the second part may be used to suppress the fundamental component using a high-pass filter. The multiple non-focused ultrasound echo signals may be wall-filtered using one or more wall filters.

In step S400, the image processing unit 7 may perform data conversion on the flow data to obtain a B-mode ultrasound image sequence.

The image processing unit 7 may perform data conversion on the flow data on which related signal processing (including enhancement and logarithmic compression, etc.) has been performed or on the wall-filtered flow data to obtain the ultrasound image sequence, which will be displayed on the display device 8.

The quadrature demodulated signal after the signal processing may include I and Q signals, which may be wall-filtered respectively. Based on the I and Q signals before and after the filtering, the following methods may be used to obtain the image data in the ultrasound imaging systems as shown in FIG. 1A and FIG. 1B.

The image processing unit 7 may calculate the variances of the I and Q data of the flow data. The variances may be used to distinguish the non-flow region and the flow region in the image. Grayscales and/or colors may be used to map the trends of the variances to obtain B-mode ultrasound image sequence overlaid with grayscales and/or colors, or obtain B-mode ultrasound image sequence on which the grayscales and/or colors are overlaid based on different regions. The regions with large variances may represent the flow, while the regions with small variances may represent stationary non-flow. The variances may be calculated using the following formula.

The variance Var may be represented as formula (1) below:

$$\text{Var} = \frac{(I_{i+1}I_i + Q_{i+1}Q_i)^2 + (Q_{i+1}I_i - I_{i+1}Q_i)^2}{I_i^2 + Q_i^2} \quad (1)$$

where i=1, ..., N, which represent the sampling time. $I_i$ represent I data at $i^{th}$ time, and $Q_i$ represent Q data at $i^{th}$ time.

The variances may also be represented as formula (2) below:

$$V_{ar} = \frac{(I_{i+1}I_i + Q_{i+1}Q_i)^2 + (Q_{i+1}I_i - I_{i+1}Q_i)^2}{I_i^2 + Q_i^2} \quad (2)$$

where K=0, 1, 2, 3 .... R(0) represents the energy of the flow signals obtained using Lag-zero method, which may be represented as formula (3) below:

$$R(0) = \sum_{i=0}^{N} \frac{I_i^2 + Q_i^2 + I_{i+k}^2 + Q_{i+k}^2}{2(N+1)};$$

The variances at corresponding locations may be calculated according to the formulas (1) or (2), and different grayscales and/or colors may be used to map the trends of the variances. Thereafter, the B-mode ultrasound images on which the grayscales and/or colors are overlaid may be obtained in the image processing unit 7 for display. For example, the variances at locations of the entire image may be mapped using grayscales. When the B-mode ultrasound image sequence obtained by overlaying the grayscales on the B-mode ultrasound image are continuously displayed, the entire images may be represented by grayscales and cloud-like clusters which are rolling may be presented in flow regions. Alternatively, the variances at locations of the entire image may be mapped using colors. When the B-mode ultrasound image sequence obtaining by overlaying the colors on the B-mode ultrasound images are continuously displayed, the entire images may be represented by colors and colored cloud-like clusters which are rolling may be presented in the flow regions. Alternatively, a variance threshold may be used to distinguish the non-flow regions and the flow regions in the image. Thereafter, the trends of the variances may be mapped with colors, thereby overlaying the colors in the flow regions in the images. Different colors may be obtained by adjusting at least one of hue, transparency, and saturation. By mapping the trends of the variances at the locations in the image with colors, the color information of the image may be obtained.

The data conversion may be performed on the wall-filtered flow data using one of the following methods to obtain the B-mode ultrasound image sequence.

The first method may be calculating the variances of the I and Q data demodulated from the wall-filtered flow data and mapping the trends of the variances with grayscales and/or colors to obtain the B-mode ultrasound image sequence. The methods for calculating the variances may be similar to the formula (1) to (3) above.

The second method may be converting the I and Q data demodulated from the wall-filtered flow data from polar coordinates to Cartesian coordinates and mapping the trends of the amplitudes of the signal envelopes over time with grayscales and/or colors to obtain the B-mode ultrasound image sequence. For example, the flow image may be expressed as Flow_image (x, z), and the B-mode ultrasound image sequence may be obtained by following formula:

$$\text{Flow\_image}(x,z) = \sqrt{I^2(x,z) + Q^2(x,z)}$$

The value of each point in the image may be obtained directly. The second method is similar to conventional B-mode imaging methods.

The third method may be calculating the energy of the signals representing the flow based on the I and Q data demodulated from the wall-filtered flow data and mapping the energy of the signals with grayscales and/or colors to obtain the B mode ultrasound image sequence. For example, the Lag-zero method may be used to obtain the energy of the flow signals, as shown by the formula (3) above.

In the case that one data exists, Hilbert transform may be performed on the RF data of the image along the depth to obtain the I and Q data. Thereafter, the wall filtering may be performed. The B-mode ultrasound image sequence may be obtained using one of the three methods described above.

The image processing unit may further calculate the energy of the signals represent the flow based on the wall-filtered flow data, determine the flow regions and non-flow regions in the ultrasound image data based on an energy threshold, and perform the data conversion on the wall-filtered flow data in the flow regions to obtain the B-mode ultrasound image sequence. This way, more clear and accurate flow information may be obtained by the obtained image data.

The energy of the signals at corresponding location may be calculated according to the formula (3), and the trends of the energy of the signals may be mapped with different grayscales and/or colors. Thereafter, the B-mode ultrasound images on which the grayscales and/or colors are overlaid may be obtained in the image processing unit 7 for display. For example, the energy at locations of the entire image may be mapped using grayscales. When the B-mode ultrasound image sequence obtaining by overlaying the grayscales on the B-mode ultrasound image are continuously displayed, the entire images may be represented by grayscales and cloud-like clusters which are rolling may be presented in the regions where the flow is flowing. Alternatively, the energy at locations of the entire image may be mapped using colors. When the B-mode ultrasound image sequence obtaining by overlaying the colors on the B-mode ultrasound images are continuously displayed, the entire images may be represented by colors and colored cloud-like clusters which are rolling may be presented in the regions where the flow is flowing. Alternatively, an energy threshold may be used to distinguish the non-flow regions and the flow regions in the image. Thereafter, the trends of the energy may be mapped with colors, thereby overlaying the colors in the flow regions in the images. Different colors may be obtained by adjusting one of hue, transparency and saturation. By mapping the trends of the energy at the locations in the image with colors, the color information of the image may be obtained.

In step S500, the display device 8 may display the B-mode ultrasound image sequence, thereby presenting the flow in flowing manner. For example, gray or colored cloud-like clusters which are rolling may be presented in the flow regions in which the flow is flowing on the display device 8.

Figure 1C:
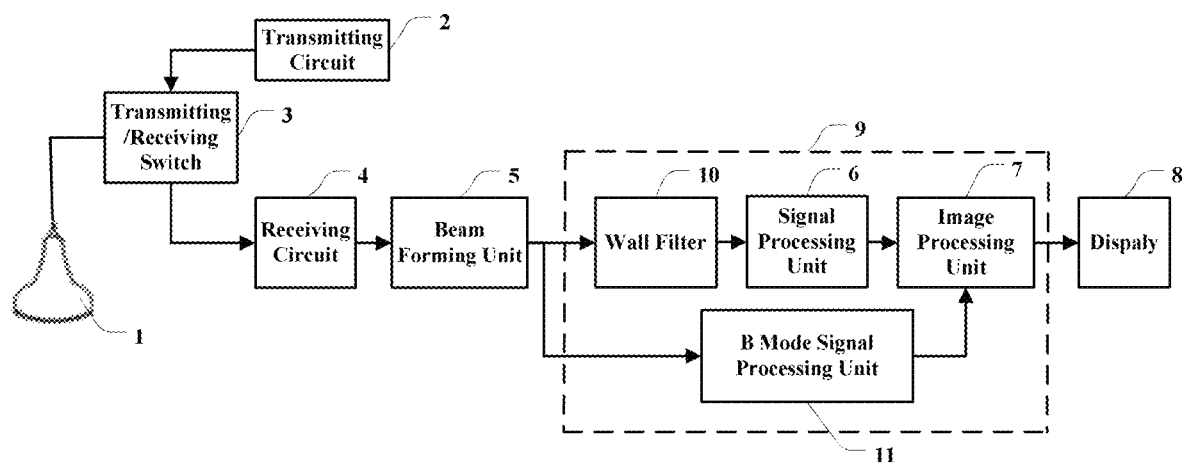

Based on the embodiments above, the ultrasound imaging system shown in FIG. 1C may further include a B-mode signal processing unit 11. The multiple groups of non-focused ultrasound echo signals may be sent to the wall filter 10 and the signal processing unit 6 to obtain the wall-filtered flow data, and also sent to the B-mode signal processing unit 11 to obtain the ultrasound image data by signal detection, signal enhancement or other processes. The image processing unit 7 may further overlay the wall-filtered flow data on the ultrasound image data and perform data conversion thereon to obtain the B-mode ultrasound image sequence. With regard to the B-mode signals processing unit 11, reference may be made to the description related to the signal processing unit 6.

Figure 7:
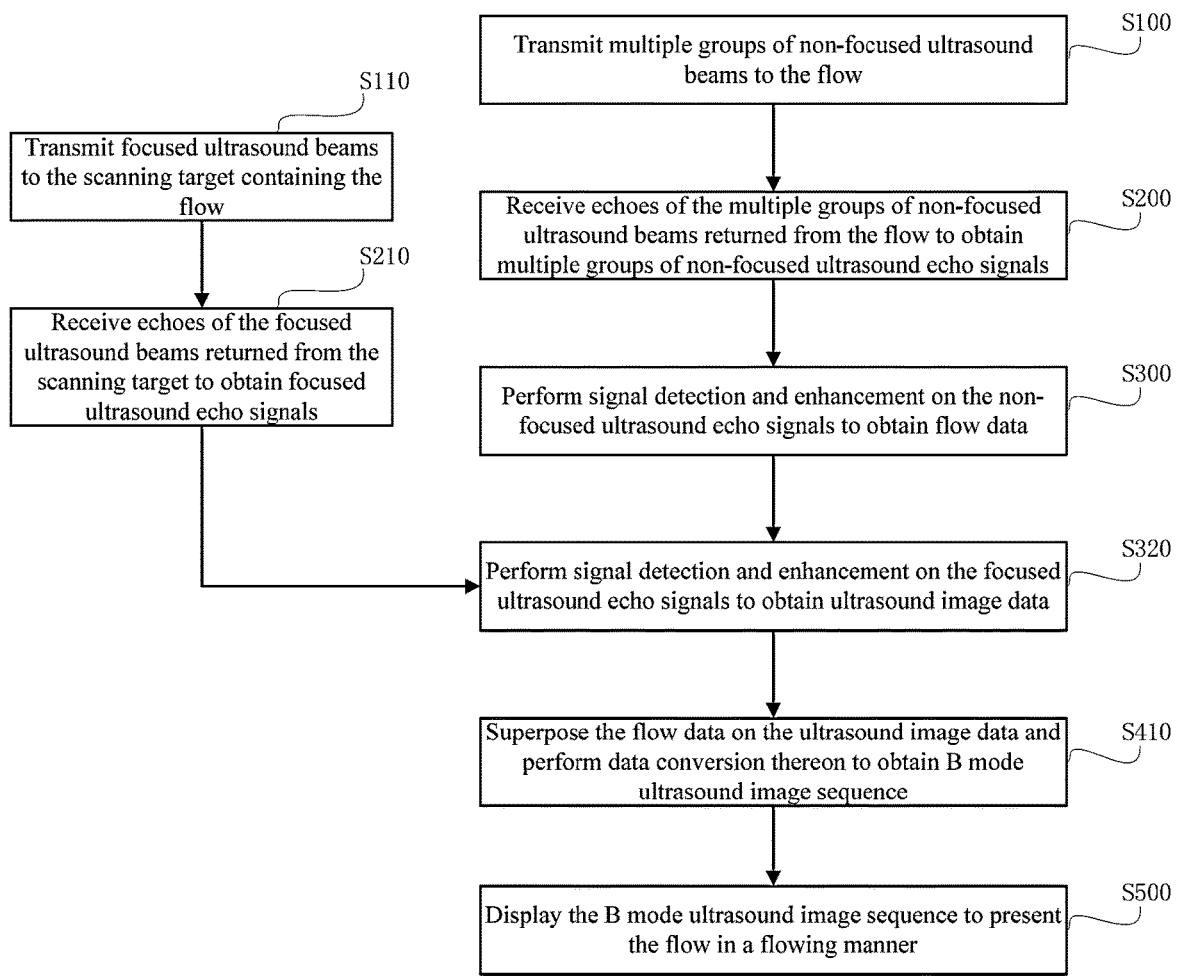
FIG. 7 is a flow chart in one embodiment.

Furthermore, in one embodiment, the focused ultrasound beam may be used to obtain background image with better quality. Therefore, an ultrasound imaging method as shown in FIG. 7 may be provided based on the ultrasound grayscale imaging system shown in FIG. 1D.

Based on step S100, a step S110 may further be provided, in which the transmitting circuit 2 may further excite the probe to transmit focused ultrasound beams to the scanning target containing the flow besides exciting the probe to transmit the multiple groups of non-focused ultrasound beams to the flow. The focused ultrasound beams here may include multiple groups of focused ultrasound beams in order to obtain multiple ultrasound images over time.

Based on step S200, a step S210 may further be provided, in which the receiving circuit 4 may receive the echoes of the focused ultrasound beams returned from the scanning target to obtain focused ultrasound echo signals. For example, the receiving circuit 4 and may receive the echoes of multiple groups of focused ultrasound beams returned from the scanning target to obtain multiple groups of focused ultrasound echo signals to generate multiple ultrasound image data over time.

When or after the step S310 is performed, step S320 may further be performed, in which the B-mode signal processing unit 11 may perform processes such as signal detection or enhancement, etc. on the focused ultrasound echo signals to obtain the ultrasound image data, thereby obtaining more clear, better B-mode images according to the focused ultrasound beams. With regard to the processing of the B-mode signal processing unit 11, reference may be made to conventional processes in which ultrasound image data is obtained based on the focused ultrasound echo signals.

In the method of FIG. 7, based on step S300 and step S320, the step S400 above may be replaced with step S410, in which the image processing unit 7 may overlay the flow data on the ultrasound image data and perform the data conversion thereon to obtain the B-mode ultrasound image sequence. In step 500, the B-mode ultrasound image sequence may be displayed on the display device 8 to present the flow.

Figure 6:
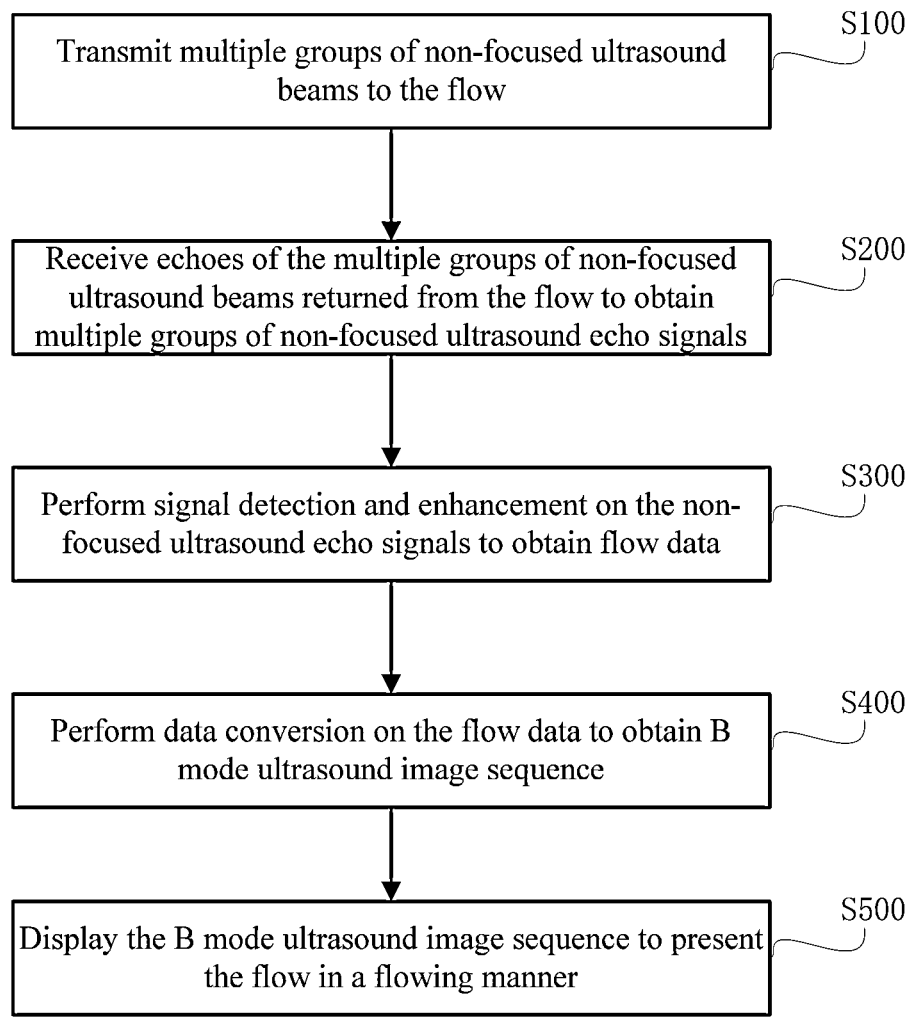
FIG. 6 is a flow chart in one embodiment.

Some steps of the methods above may be the same or similar to those of the methods in FIG. 6. With regard to the processing related to the echo signals of the focused ultrasound beams, reference may be made to conventional processing related to focused ultrasound beams.

In one embodiment, the frame rate may be relatively low when the focused ultrasound beams are used. However, since the energy of the focused ultrasound beams is concentrated and the imaging is performed at the concentration location, the obtained echo signals may have high signal-to-noise ratio, and ultrasound images with better quality may be obtained. Therefore, in one embodiment, the combination of different kinds of ultrasound beams may be used in order to solve the problems of distortion in imaging the flow with high velocity in grayscale flow imaging and low time resolution of the ultrasound images. When both focused ultrasound beams and non-focused ultrasound beams are used, the focused ultrasound beams and the non-focused ultrasound beams may be transmitted alternately in order to keep the acquisition of the flow signals and the B-mode ultrasound image data synchronized in time as much as possible.

In addition, the transmitting circuit 2 may excite the probe 1 to transmit multiple focused ultrasound beams with different transmission angles to the scanning target containing the flow. The echoes of the multiple focused ultrasound beams with different transmission angles may be used to obtain one frame of ultrasound image. Therefore, echo signals with higher signal-to-noise ratio may be acquired and ultrasound image data with better quality may be obtained while the imaging frame rate is guaranteed.

In one embodiment, multiple non-focused ultrasound beams and focused ultrasound beams with different transmission angles may be transmitted alternately. For example, the non-focused ultrasound beams and the focused ultrasound beams may be transmitted to the scanning target containing the flow alternately according to the transmission angles. In the same transmission cycle, multiple non-focused ultrasound beams with different transmission angles may be transmitted to the flow, and thereafter, multiple focused ultrasound beams with different transmission angles may be transmitted to the scanning target containing the flow. Alternatively, the non-focused and focused ultrasound beams with the same transmission angle may be successively transmitted to the flow and the scanning target containing the flow, and thereafter, this cycle may be repeated for multiple times to achieve the transmission of the multiple non-focused and focused ultrasound beams.

Figure 1D:
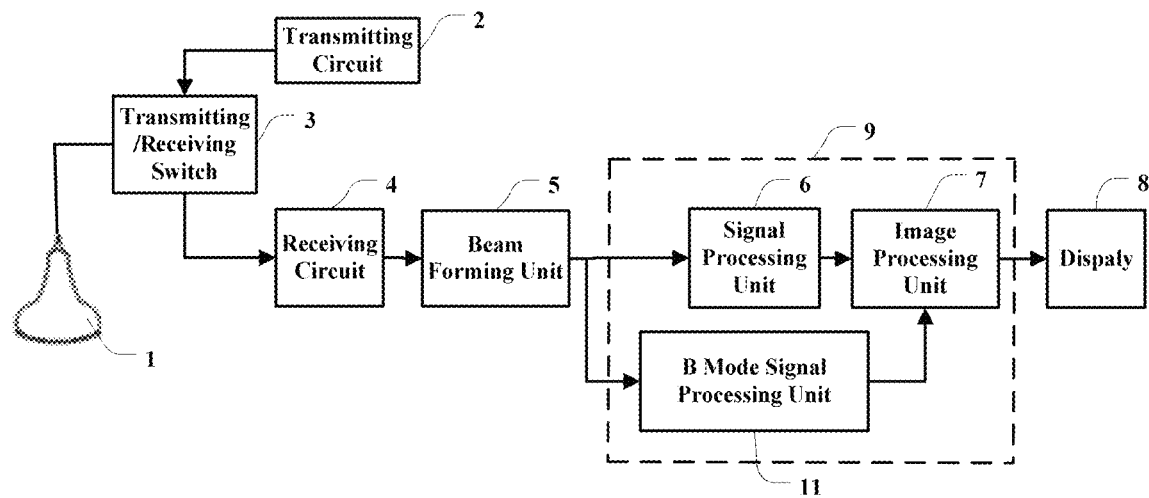

The system shown in FIG. 1D may further be provided with a wall filter 10 to form the ultrasound grayscale imaging system shown in FIG. 1C. Therefore, in step S410 in FIG. 7, the image processing unit 7 may overlay the wall-filtered flow data on the ultrasound images and perform the data conversion thereon to obtain the B-mode ultrasound image sequence. With regard to the processing performed by the wall filter 10 to the echoes of the non-focused ultrasound beams, reference may be made to the description of the step S300 above, which will not be described again herein.

In the ultrasound imaging systems of the embodiments shown in FIG. 1C and FIG. 1D, the frequency of the signals outputted by the beam former may generally be moved to base band by a demodulator. One method for implementing this process may be multiplying the input signals by a complex sinusoidal signal ej2πfdt, where fd is the frequency shift amount from the frequency of the signals to the base band. The demodulated signals may be sent to the signal processing unit 6 and the image processing unit 7, thereby converting the demodulated signals into corresponding image data. In B-mode (grayscale), some additional processing may be performed, such as edge enhancement and logarithmic compression of the signal envelope. The image processing unit may overlay the data from the signal processing unit 6 and the B-mode signal processing unit 11 to obtain the desired images. Particularly, an image overlay unit may convert the image data in polar coordinates (R-θ) or Cartesian coordinates into display image data in Cartesian coordinates which is properly calibrated and suitable for the video rate. Thereafter, the scan-converted data may be displayed on the display device 8. The display device may display the time-varying amplitudes of the envelopes of the B-mode signals as grayscale. With each transmitted beam, one scanning line may correspondingly be obtained.

In one embodiment, the data obtained by wall filtering may be the flow data. The flow data may be overlaid on the ultrasound images, and thereafter, the images may be displayed, thereby presenting the flowing state of the blood flow. Different weights may be used during the superposition. Alternatively, based on the energy of the flow, a suitable energy threshold may be used to distinguish the flow regions and the non-flow regions. In the flow regions, the wall-filtered images may be displayed, while in the non-flow regions, the ultrasound images not being wall-filtered may be displayed. Therefore, when the flow data overlaid on the ultrasound image data is displayed, the energy of the signals representing the flow may be calculated based on the wall-filter flow data and the flow regions and the non-flow regions in the ultrasound images obtained according to the focused ultrasound beams may be determined based on an energy threshold. Thereafter, the wall-filtered flow data may be overlaid on the flow regions and the data conversion may be performed thereon to obtain the B-mode ultrasound image sequence.

FIGS. 6 and 7 are flow charts of the ultrasound grayscale imaging method in one embodiment. It should be understood that, although the steps in the flow chart in FIGS. 6 and 7 are presented successively according to the arrows, these steps will not be successively performed necessarily in the order indicated by the arrows. Unless expressly stated by the present disclosure, these steps will not be limited to a strict order, but can be performed in any order. Furthermore, at least a part of the steps in FIGS. 6 and 7 may include multiple sub-steps or multiple stages. These sub-steps or stages will not necessarily be performed at the same time, but can be performed in different time. These sub-steps or stages will not necessarily be performed successively, but can be performed alternatively with other steps or at least a part of the sub-steps or stages of other steps. In the embodiments above, only the steps shown in FIGS. 6 and 7 are described. However, in the case of no logical conflict, the embodiments above may be combined with each other to form new technical solutions, which shall still be in the scope of the present disclosure.

According to the description of the embodiment above, a person skilled in the art will understand that the methods in the embodiments above may be implemented by universal hardware platform with software. Alternatively, they may be implemented by hardware. The software may be stored in a non-transitory computer-readable storage medium (e.g., ROM, disk, disc or cloud space in server), and may include instructions which can enable a terminal equipment (which may be cell phone, computer, sever or network equipment, etc.) to implement the systems and methods of the embodiments of the present disclosure.

In the embodiments of the present disclosure, improvements have been provided based on conventional grayscale flow imaging technologies. Non-focused ultrasound beams or combination of non-focused and focused ultrasound beams may be used. Multiple scan lines or one frame of image may be obtained by one transmission. This way, the frame rate may be increased by 10-100 times compared with traditional methods. The acquired signals may be wall-filtered to obtain the flow data, therefore there is no issue of filter transient compared with traditional line-by-line scanning in which each line need to be scanned for several times. Each frame of the images obtained by non-focused ultrasound beam (e.g., plane beam) may be obtained continuously and therefore the transient issue need not to be considered when filtering. Furthermore, multiple frames of images may be used to perform the wall filtering without loss in frame rate.

This disclosure has been made with reference to various exemplary embodiments. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. An ultrasound grayscale flow imaging system, comprising:
    a probe;
    a transmitting circuit which excites the probe to transmit multiple groups of non-focused ultrasound beams and focused ultrasound beams to a scanning target containing a flow, wherein the non-focused ultrasound beams and focused ultrasound beams comprise only B-mode pulses;
    a receiving circuit which receives echoes of the multiple non-focused ultrasound beams returned from the flow to obtain multiple groups of non-focused ultrasound echo signals and receives echoes of the multiple focused ultrasound beams returned from the scanning target to obtain multiple groups of focused ultrasound echo signals;
    a signal processing unit which obtains grayscale flow data according to the multiple groups of non-focused ultrasound echo signals using grayscale flow imaging without using Doppler processing;
    a B-mode signal processing unit which obtains grayscale ultrasound image data according to the multiple groups of focused ultrasound echo signals;
    an image processing unit which overlays the grayscale flow data on the grayscale ultrasound image data and obtains a B-mode ultrasound image sequence according to the grayscale ultrasound image data overlaid with the grayscale flow data, wherein the image processing unit is further configured to:
        calculate variances of I data and Q data demodulated from the grayscale flow data, wherein the variances are calculated according to the formula, $$V_{ar} = \frac{\left(\sum_{i=0}^{N} I_{i+k}I_i + Q_{i+k}Q_i\right)^2 + \left(\sum_{i=0}^{N} Q_{i+k}I_i - I_{i+k}Q_i\right)^2}{R(0)}$$

where i represents a sampling time, $I_i$ represents I data at $i^{th}$ time, and $Q_i$ represents Q data at $i^{th}$ time;
        determine non-flow regions and flow regions based on a variance threshold; and
        map trends of the variances with grayscales and/or colors to obtain the B-mode ultrasound image sequence overlaid with the grayscales and/or colors or obtain the B-mode ultrasound image sequence overlaid with the grayscales and/or colors based on regions; and
    a display device which displays the B-mode ultrasound image sequence.

2. The ultrasound grayscale flow imaging system of claim 1, wherein the focused ultrasound beams and the non-focused ultrasound beams are transmitted alternately.

3. The ultrasound grayscale flow imaging system of claim 1, wherein the transmitting circuit adjusts a time delay of each transducer of the probe such that each successive non-focused ultrasound beam has a different virtual focus that is behind the probe.

4. The ultrasound grayscale flow imaging system of claim 3, wherein the non-focused ultrasound beams at least partially overlap, and wherein the signal processing unit is to spatially compound the non-focused ultrasound echo signals received from the at least partially overlapping non-focused ultrasound beams.

5. The ultrasound grayscale flow imaging system of claim 3, wherein all transducers of the probe are used to generate the non-focused ultrasound beams.

6. The ultrasound grayscale flow imaging system of claim 1, wherein the transmitting circuit adjusts a time delay of each transducer of the probe such that each successive non-focused ultrasound beam has a different transmission angle.

7. The ultrasound grayscale flow imaging system of claim 6, wherein the focused ultrasound beams and the non-focused ultrasound beams with different transmission angles are transmitted alternately.

8. The ultrasound grayscale flow imaging system of claim 6, wherein the signal processing unit is to spatially compound the non-focused ultrasound echo signals received from the successive non-focused ultrasound beams with different transmission angles.

9. The ultrasound grayscale flow imaging system of claim 1, wherein the transmitting circuit adjusts a time delay of each transducer of the probe to generate a diffuse beam that diverges from the probe, and wherein the multiple groups of non-focused ultrasound beams comprise multiple diffuse beams.

10. The ultrasound grayscale flow imaging system of claim 1, further comprising:
a wall filter to perform wall filtering on the multiple groups of non-focused ultrasound echo signals and send the wall-filtered multiple groups of non-focused ultrasound echo signals to the signal processing unit to obtain wall-filtered grayscale flow data;
wherein the image processing unit overlays the wall-filtered grayscale flow data on the grayscale ultrasound image data and obtains the B-mode ultrasound image sequence according to the grayscale ultrasound image data overlaid with the wall-filtered grayscale flow data.

11. The ultrasound grayscale flow imaging system of claim 1, wherein each flow region is determined to have a variance above a variance threshold.

12. The ultrasound grayscale flow imaging system of claim 1, wherein the image processing unit obtains the B-mode ultrasound image sequence by converting I data and Q data demodulated from wall-filtered grayscale flow data from polar coordinates to Cartesian coordinates and mapping trends of amplitudes of signal envelopes over time with grayscales and/or colors to obtain the B-mode ultrasound image sequence.

13. The ultrasound grayscale flow imaging system of claim 12, wherein the B-mode ultrasound image sequence is obtained using the formula:

$$\text{flow\_image}(x,z) = \sqrt{I^2(x,z) + Q^2(x,z)}$$

where flow_image(x,z) is an expression of a grayscale flow image.

14. The ultrasound grayscale flow imaging system of claim 10, wherein the image processing unit is further configured to:
calculate energy of signals representing the flow based on wall-filtered grayscale flow data;
determine flow regions and non-flow regions in the grayscale ultrasound image data based on an energy threshold;
overlay the wall-filtered grayscale flow data on the flow regions; and
obtain the B-mode ultrasound image sequence according to the grayscale ultrasound image data overlaid with the wall-filter grayscale flow data.

15. The ultrasound grayscale flow imaging system of claim 1, wherein each non-focused ultrasound beam covers an entire area to be scanned.

16. An ultrasound grayscale flow imaging method, comprising:
transmitting, via a probe, multiple groups of non-focused ultrasound beams and focused ultrasound beams to a scanning target containing a flow, wherein the non-focused and focused ultrasound beams comprise only B-mode pulses;
receiving echoes of the multiple non-focused ultrasound beams returned from the flow to obtain multiple groups of non-focused ultrasound echo signals and receiving echoes of the multiple focused ultrasound beams returned from the scanning target to obtain multiple groups of focused ultrasound echo signals;
obtaining grayscale flow data according to the multiple groups of non-focused ultrasound echo signals using grayscale flow imaging without using Doppler processing;
obtaining B-mode ultrasound image data according to the multiple groups of focused ultrasound echo signals;
overlaying the grayscale flow data on the B-mode ultrasound image data to obtain a B-mode ultrasound image sequence by:
calculating variances of I data and Q data demodulated from the grayscale flow data, wherein the variances are calculated according to the formula, $$V_{ar} = \frac{(I_{i+1}I_i + Q_{i+1}Q_i)^2 + (Q_{i+1}I_i - I_{i+1}Q_i)^2}{I_i^2 + Q_i^2}$$

where i represents a sampling time, $I_i$ represents I data at $i^{th}$ time, and $Q_i$ represents Q data at $i^{th}$ time;
determining non-flow regions and flow regions based on a variance threshold; and
mapping trends of the variances with grayscales and/or colors to obtain the B-mode ultrasound image sequence overlaid with the grayscales and/or colors or obtain the B-mode ultrasound image sequence overlaid with the grayscales and/or colors based on regions; and
displaying the B-mode ultrasound image sequence.

17. The ultrasound grayscale flow imaging method of claim 16, wherein:
each non-focused ultrasound beam covers an entire area to be scanned;
all transducers of the probe are used to generate each non-focused ultrasound beam;
transmitting comprises adjusting a time delay of each transducer of the probe such that each successive non-focused ultrasound beam has a different virtual focus that is behind the probe;
the non-focused ultrasound beams at least partially overlap; and
obtaining the grayscale flow data comprises spatially compounding the non-focused ultrasound echo signals received from the at least partially overlapping non-focused ultrasound beams.

18. An ultrasound grayscale flow imaging system, comprising:
a probe;
a transmitting circuit which excites the probe to transmit multiple groups of non-focused ultrasound beams and focused ultrasound beams to a scanning target containing a flow, wherein the non-focused ultrasound beams and focused ultrasound beams comprise only B-mode pulses;
a receiving circuit which receives echoes of the multiple non-focused ultrasound beams returned from the flow to obtain multiple groups of non-focused ultrasound echo signals and receives echoes of the multiple focused ultrasound beams returned from the scanning target to obtain multiple groups of focused ultrasound echo signals;
a signal processing unit which obtains grayscale flow data according to the multiple groups of non-focused ultrasound echo signals using grayscale flow imaging without using Doppler processing;
a B-mode signal processing unit which obtains grayscale ultrasound image data according to the multiple groups of focused ultrasound echo signals;
an image processing unit which overlays the grayscale flow data on the grayscale ultrasound image data and obtains a B-mode ultrasound image sequence according to the grayscale ultrasound image data overlaid with the grayscale flow data, wherein the image processing unit is further configured to:

calculate variances of I data and Q data demodulated from the grayscale flow data, wherein the variances are calculated according to the formula, $$V_{ar} = \frac{\left(\sum_{i=0}^{N} I_{i+k}I_i + Q_{i+k}Q_i\right)^2 + \left(\sum_{i=0}^{N} Q_{i+k}I_i - I_{i+k}Q_i\right)^2}{R(0)}$$

where K=0, 1, 2, 3 . . . R(0) represents energy of flow signals obtained using a Lag-zero method, which is represented by:

$$R(0) = \sum_{i=0}^{N} \frac{I_i^2 + Q_i^2 + I_{i+k}^2 + Q_{i+k}^2}{2(N+1)};$$

determine non-flow regions and flow regions based on a variance threshold; and map trends of the variances with grayscales and/or colors to obtain the B-mode ultrasound image sequence overlaid with the grayscales and/or colors or obtain the B-mode ultrasound image sequence overlaid with the grayscales and/or colors based on regions; and a display device which displays the B-mode ultrasound image sequence.

* * * * *